United States Patent [19]

Ichihashi et al.

[11] Patent Number: 4,665,274

[45] Date of Patent: May 12, 1987

[54] METHOD FOR PRODUCING CYCLOOLEFINS

[75] Inventors: Hiroshi Ichihashi; Hiroshi Yoshioka, both of Niihama, Japan

[73] Assignee: Sumitomo Chemical Company, Limited, Osaka, Japan

[21] Appl. No.: 900,846

[22] Filed: Aug. 27, 1986

[30] Foreign Application Priority Data

Sep. 11, 1985 [JP] Japan .................. 60-200899

[51] Int. Cl.$^4$ ................................. C07C 5/11
[52] U.S. Cl. .................... 585/267; 585/266; 585/273; 585/276
[58] Field of Search .......... 585/266, 267, 273, 274, 585/276

[56] References Cited

U.S. PATENT DOCUMENTS

| | | | |
|---|---|---|---|
| 3,391,206 | 7/1968 | Beck | 585/273 |
| 4,197,415 | 4/1980 | Hideyuki et al. | 585/267 |
| 4,225,733 | 9/1980 | Kameyama et al. | 585/266 |
| 4,392,001 | 7/1983 | Don et al. | 585/273 |
| 4,495,373 | 1/1985 | Niwa et al. | 585/267 |
| 4,503,249 | 3/1985 | Nowack et al. | 585/274 |
| 4,575,572 | 3/1986 | Ichihashi et al. | 585/266 |

FOREIGN PATENT DOCUMENTS

| | | | |
|---|---|---|---|
| 764502 | 8/1957 | Canada | 585/266 |
| 0170915 | 2/1986 | European Pat. Off. | |
| 3046939 | 10/1976 | Japan | 585/266 |
| 3063350 | 11/1976 | Japan | 585/273 |
| 9186932 | 4/1983 | Japan | 585/273 |

*Primary Examiner*—Asok Pal
*Attorney, Agent, or Firm*—Stevens, Davis, Miller & Mosher

[57] ABSTRACT

A method for producing cycloolefins, useful as an intermediate for lysine, caprolactam, adipic acid etc., by the partial hydrogenation of corresponding aromatic hydrocarbons with a hydrogen gas in the presence of water and a catalyst comprising barium sulfate as a carrier and ruthenium and one or more metals selected from the group consisting of iron, cobalt, silver and copper supported on the carrier, characterized by incorporating one or more metal oxides selected from the group consisting of silicon dioxide, titanium dioxide and aluminum oxide in the reaction system.

11 Claims, No Drawings

METHOD FOR PRODUCING CYCLOOLEFINS

The present invention relates to a method for producing cycloolefins by the partial hydrogenation of corresponding aromatic hydrocarbon compounds.

Cycloolefins are an important intermediate material for lysine, caprolactam, adipic acid, medicines, agricultural chemicals, etc., being a useful compound.

For producing cycloolefins, there are so far known many methods such as dehydration of cyclohexanols, dehydrohalogenation of halogenated cyclohexanes, cracking of cyclohexylallenes, dehydrogenation or oxidative dehydrogenation of cyclohexanes, etc.

It is well known that to produce cyclolefins in good yields by the partial hydrogenation of aromatic hydrocarbon compounds is difficult because the cycloolefins formed are generally easier to react than are the aromatic hydrocarbon compounds, a material.

In any of the prior-art methods described above, the starting materials are compounds derived from aromatic hydrocarbon compounds, and therefore, if it is possible to obtain cycloolefins in good yields directly from aromatic hydrocarbon compounds by the partial hydrogenation thereof, such process is the most simplified one, being preferred from the industrial point of view.

The following methods are well known to produce cycloolefins by the partial hydrogenation of aromatic compounds:

(1) A method of partial hydrogenation in the presence of water, an alkali agent and a catalyst containing the cation of at least one element belonging to Group VIII of the periodic table (U.S. Pat. No. 3,767,720).

(2) A method of partial hydrogenation in the presence of a catalyst comprising a compound containing at least one rare earth element and ruthenium supported thereon [Japanese Patent Application Kokai (Laid-open) No. 186,932/1984].

(3) A method of partial hydrogenation in the presence of water and a ruthenium-silica catalyst prepared by hydrolyzing a mixed solution of ruthenium glykoxide and ethyl silicate, followed by reduction with hydrogen at 400° C. [Japanese Patent Application Kokai (Laid-open) No. 155,328/1984].

(4) A method of partial hydrogenation in the presence of water, cobalt sulfate and a catalyst comprising a metal oxide (e.g. silica, alumina) and mainly ruthenium supported thereon [Japanese Patent Application Kokai (Laid-open) No. 130,926/1982].

(5) A method of partial hydrogenation under a neutral or acid condition in the presence of water and a catalyst comprising alumina or zinc aluminate which is a carrier and ruthenium and at least one member selected from iron, cobalt, nickel, chromium, tungsten and molybdenum supported on the carrier (U.S. Pat. No. 3,912,787).

The method (1) not only requires a very complicated reaction system, but also has problems such as separation of reaction products, corrosion of reactors by chlorine ions, etc., so that this method may not always be said to be satisfactory from the industrial point of view.

The method (2) produces cycloolefins in relatively good yields, but there is a need to add large amounts of alkali agent to the reaction system. The methods (3), (4) and (5) are required for great improvements in selectivity and yield, so that it was difficult to put them to practical use in industry.

Previously, the present inventors proposed in U.S. Pat. No. 4,575,572 a method of partial hydrogenation in the presence of water and a catalyst comprising barium sulfate which is a carrier and metal components consisting mainly of futhenium supported on the carrier. It was however found that the selectivity of cycloolefins was greatly improved by this method, but that the life of the catalyst was insufficient.

An object of the present invention is to solve the defects of these prior arts, thereby providing an industrially advantageous method for producing cycloolefins.

In order to attain this object, the present inventors made an extensive study and found a novel method suitable for producing cycloolefins by the partial hydrogenation of corresponding aromatic hydrocarbons. The present inventors thus attained to the present invention.

The present invention provides a method for producing cycloolefins by the partial hydrogenation of corresponding aromatic hydrocarbons with a hydrogen gas in the presence of water and a catalyst comprising barium sulfate as a carrier and metal components consisting mainly of ruthenium supported on the carrier, characterized by incorporating one or more metal oxides selected from the group consisting of silicon dioxide, titanium dioxide and aluminum oxide in the reaction system.

The method of the present invention will be explained in more detail.

The aromatic hydrocarbons, which are an object of the present invention, include benzene, toluene, xylene, lower alkylbenzene, etc. These aromatic hydrocarbons need not have particularly a high purity, and it doesn't matter if they contain cycloparaffins, lower paraffinic hydrocarbons, etc.

The catalyst used in the present invention is the so-called supported catalyst comprising barium sulfate which is a carrier and ruthenium supported on the carrier, but other metal components than ruthenium may be co-supported together with ruthenium.

The metal components to be co-supported on the carrier include one or more metals selected from the group consisting of iron, cobalt, silver, copper, etc. Also, one or more metal oxides to be incorporated in the reaction system selected from the group consisting of silicon dioxide, titanium dioxide and aluminum oxide may be added in the form of a multi-component carrier by mixing with barium sulfate during preparation of the catalyst, or may be added alone to the reaction system separately from the catalyst.

Preparation of the catalyst is carried out according to the commonly used preparation methods for supported metal catalysts. For such methods, the following well-known impregnation/supporting methods are preferably used: Vaporization/drying methods in which a carrier is dipped in a metal compound-containing solution, and the solvent is vaporized with stirring to fix the metal compound to the carrier; spraying methods in which a metal compound-containing solution is sprayed onto a carrier being kept in a dry state; and methods in which a carrier is dipped in a metal compound-containing solution and then filtered off, etc.

The ruthenium compound used includes halides, nitrates, hydroxides and oxides of ruthenium, complexes (e.g. ruthenium carbonyl, ruthenium ammine complex), ruthenium alkoxides, etc.

Compounds providing the co-supported metals include halides, nitrates, etc. of the metals. Solvents for these metal compounds include water and organic solvents such as alcohol, acetone, tetrahydrofuran, etc., and they may be used alone or in combination. These metal compounds are fixed to the carrier by the methods described above and activated by reduction.

For the reducing agent, hydrogen, carbon monoxide, alcohol vapor, hydrazine, sodium borohydride and other well-known reducing agents may be used.

When hydrogen is used, a reduction temperature in the range of from 150° to 450° C., preferably from 180° to 300° C. is selected. When the reduction temperature is lower than 150° C., the reduction of ruthenium compounds is not sufficient. When the reduction temperature is higher than 400° C., supported ruthenium forms aggregates to cause a reduction in the metal surface area and the change in property of the catalyst surface, which result in reduction in the activity and selectivity of the catalyst to form cycloolefins.

The amount of supported ruthenium is in the range of from 0.01 to 20 wt.%, preferably from 0.1 to 10 wt.% based on the total amount of the carrier and ruthenium.

When iron or cobalt is used as a co-supported component, its atomic ratio to ruthenium is in the range of from 0.1 to 15.0, preferably from 0.5 to 5.0. When copper or silver is used as such component, its atomic ratio to ruthenium is in the range of from 0.05 to 5.0, preferably from 0.1 to 1.0.

When one or more metal oxides selected from the group consisting of silicon dioxide, titanium dioxide and aluminum oxide are added to the reaction system separately from the catalyst, the proportion of metal oxide to barium sulfate-supported catalyst is in the range of from about 0.2 to about 10, preferably from 0.5 to 5 by weight ratio. When the proportion is less than about 0.2 by weight ratio, the catalyst life-lengthening effect is too low to display a sufficient catalytic effect. While, when the proportion is as large as about 10 by weight ratio, the selectivity of cyclohexene is unpreferably lowered.

The metal oxides may be added in the form of a multicomponent carrier by mixing with barium sulfate. The mixing ratio of metal oxide to barium sulfate is in the range of from about 0.2 to about 4, preferably from 0.4 to 2 by weight ratio. When the mixing ratio is less than about 0.2 by weight ratio, the catalyst life-lengthening effect is low, and when it is as large as about 4 by weight ratio, the selectivity of cyclehexene is unpreferably lowered.

In the method of the present invention, water is added to the reaction system. Since the catalyst forms a suspension in water, addition of water not only facilitates the separation of the catalyst from the reaction product in the organic layer, but also exhibits a remarkable effect in raising the selectivity of cycloolefins. The amount of water added is in the range of, generally, from 0.01 to 10 times preferably from 0.1 to 5 times by volume ratio to the aromatic hydrocarbon.

In practicing the present invention, other additives may be added if necessary. Such additives include sulfates of one or more metals selected from the group consisting of lithium, cobalt, iron and zinc. The concentration of said metal sulfates is in the range of 1:1 to 1:500, preferably 1:5 to 1:250, as expressed by the atomic ratio of the metal species to ruthenium in the catalyst used for reaction.

The hydrogen pressure at reaction is in the range of, generally, from 0.1 to 20 MPa, preferably from 0.5 to 10 MPa. Higher pressures than 20 MPa are uneconomical from the industrial viewpoint, and lower pressures than 0.1 MPa slow down the reaction rate, being also uneconomical in terms of apparatus.

The reaction temperature is in the range of, generally, from 50° to 250° C., preferably from 100° to 200° C. Reaction temperatures higher than 250° C. lower the selectivity of cycloolefins, while reaction temperatures lower than 50° C. unpreferably slow down the reaction rate.

The form of reaction of the present invention may be any of batch systems with one or more reactors and continuous ones, there being no particular limitation to it.

According to the method of the present invention, cycloolefins can be obtained in high yields, the life of the catalyst is markedly lengthened, repeated use of the catalyst becomes possible and stable operation can be continued over a long period of time.

In order to illustrate the present invention more clearly, the following examples and comparative examples will be given. But, the present invention is not limited to these examples.

Hereupon, the conversion and selectivity shown in the examples and comparative examples are defined by the following equations:

$$\text{Conversion (\%)} = \frac{\text{Number of moles of aromatic hydrocarbon consumed by reaction}}{\text{number of moles of aromatic hydrocarbon supplied to reaction}} \times 100$$

$$\text{Selectivity (\%)} = \frac{\text{Number of moles of cycloolefins formed}}{\text{number of moles of aromatic hydrocarbon consumed by reaction}} \times 100$$

EXAMPLE 1

To a 500 c.c. eggplant-form flask were added 200 c.c. of water, 0.190 g of $RuCl_3 \cdot 3H_2O$, 0.212 g of $Co(NO_3)_2 \cdot 6H_2O$ and 0.018 g of $Cu(NO_3)_2 \cdot 3H_2O$ to dissolve the metal salts in the water. After adding 1.8 g of $BaSO_4$ and 1.8 g of $SiO_2$, the flask was equipped with a rotary evaporator. The contents of the flask were kept at room temperature for 1 hour and then at 60° C. for 1 hour with stirring to impregnate $BaSO_4$ and $SiO_2$ with the aqueous metal salt solution, and then heated to 80° C. under reduced pressure to vaporize water.

The resulting vaporization-dried product was packed in a Pyrex glass tube of 5 mm in internal diameter, heated to 200° C. while passing hydrogen at a rate of 100 c.c./min and kept at this temperature for 8 hours to activate the catalyst. The composition of the catalyst obtained was $Ru\text{-}Co\text{-}Cu/SiO_2\text{-}BaSO_4$, the Ru concentration of the catalyst being 2 wt.%, the atomic ratio of Ru:Co:Cu being 1:1:0.1 and the weight ratio of $SiO_2$ to $BaSO_4$ being 1.0.

Fifty c.c. of water was added to a 100 c.c. stainless steel autoclave in which the air was sufficiently replaced by argon in advance, and 500 mg of the above catalyst and 15 c.c. of benzene were added in this order. Thereafter, reaction was carried out with stirring at a temperature of 160° C. for 1 hour under a reaction pressure of 4.0 MPa while introducing a hydrogen gas. After completion of the reaction, the autoclave was cooled, the oily layer only was taken out and the products were analyzed by gas chromatography.

Second reaction was carried out by adding 15 c.c. of fresh benzene to the autoclave and operating the autoclave at 160° C. for 1 hour under a reaction pressure of 4.0 MPa in the same manner as above.

This operation was repeated to carry out a catalyst life-evaluating test. The results of the 1st, 5th and 10th reactions are shown in Table 1.

EXAMPLE 2

To a 500 c.c. eggplant-form flask were added 200 c.c. of water, 0.190 g of $RuCl_3 \cdot 3H_2O$ and 0.587 g of $Fe(NO_3)_3 \cdot 9H_2O$ to dissolve the metal salts in the water. After adding 1.8 g of $BaSO_4$ and 1.8 g of $SiO_2$, the flask was equipped with a rotary evaporator. Procedure was then carried out in the same manner as in Example 1 to produce a $Ru-Fe/BaSO_4-SiO_2$ catalyst (Ru concentration, 2 wt.%; and Ru:Fe atomic ratio, 1:2). Using this catalyst, the catalyst life-evaluating test was carried out according to the same procedure as in Example 1. The results are shown in Table 1.

EXAMPLE 3

Procedure was carried out in the same manner as in Example 2 except that 0.062 g of $AgNO_3$ was added in place of $Fe(NO_3)_3 \cdot 9H_2O$, to produce a $Ru-Ag/BaSO_4-SiO_2$ catalyst (Ru concentration, 2 wt.%; and Ru:Ag atomic ratio, 1:0.5). Using this catalyst, the catalyst life-evaluating test was carried out according to the same procedure as in Example 2. The results are shown in Table 1.

COMPARATIVE EXAMPLE 1

Procedure was carried out in the same manner as in Example 1 except that, in the course of catalyst preparation, 3.6 g of $BaSO_4$ only was added without adding $SiO_2$, to produce a $Ru-Co-Cu/BaSO_4$ catalyst containing no $SiO_2$ (Ru concentration, 2 wt.%; and Ru:Co:Cu atomic ratio, 1:1:0.1). Using this catalyst, the catalyst life-evaluating test was carried out according to the same procedure as in Example 1. The results are shown in Table 1.

After adding 1.8 g of $BaSO_4$ and 1.8 g of $TiO_2$, the flask was equipped with a rotary evaporator. The contents of the flask was kept at room temperature for 1 hour and then at 60° C. for 1 hour with stirring to impregnate $BaSO_4$ and $TiO_2$ with the aqueous $RuCl_3$ solution, and then heated to 80° C. under reduced pressure to vaporize water. The resulting vaporization-dried product was packed in a Pyrex glass tube of 5 mm in internal diameter, heated to 200° C. while passing hydrogen at a rate of 100 c.c./min and kept at this temperature for 8 hours to activate the catalyst. The composition of the catalyst obtained was $Ru/TiO_2-BaSO_4$ (Ru concentration, 2 wt.%; and $TiO_2:BaSO_4$ weight ratio, 1).

Fifty c.c. of water was added to a 100 c.c. stainless steel autoclave in which the air was sufficiently replaced by argon in advance, and 0.5 g of $CoSO_4 \cdot 7H_2O$, an additive, was added to dissolve it in the water. Further, 500 mg of the above catalyst and 15 c.c. of benzene were added in this order. Reaction was then carried out with stirring at a temperature of 160° C. for 1 hour under a reaction pressure of 4.0 MPa while introducing a hydrogen gas.

The results of the catalyst life-evaluating test are shown in Table 2.

EXAMPLE 5

Procedure was carried out in the same manner as in Example 4 except that, in the course of catalyst preparation, $Al_2O_3$ (produced by calcination in air at 450° C. for 3 hours) was used in place of $TiO_2$, to produce a $Ru/Al_2O_3-BaSO_4$ catalyst (Ru concentration, 2 wt.%; and $Al_2O_3:BaSO_4$ weight ratio, 1).

Using this catalyst, the catalyst life-evaluating test was carried out according to the same procedure as in Example 4. The results are shown in Table 2.

COMPARATIVE EXAMPLE 2

Procedure was carried out in the same manner as in Example 4 except that, in the course of catalyst preparation, 3.6 g of $BaSO_4$ only was added without adding $TiO_2$, to produce a 2% $Ru/BaSO_4$ catalyst.

Using this catalyst, the catalyst life-evaluating test

TABLE 1

|  | First reaction | | Fifth reaction | | Tenth reaction | |
| --- | --- | --- | --- | --- | --- | --- |
|  | Conversion of benzene (%) | Selectivity of cyclo-hexene (%) | Conversion of benzene (%) | Selectivity of cyclo-hexene (%) | Conversion of benzene (%) | Selectivity of cyclo-hexene (%) |
| Example 1 | 76.5 | 27.6 | 75.8 | 28.1 | 74.1 | 29.8 |
| Example 2 | 64.8 | 24.3 | 65.4 | 23.1 | 62.8 | 26.7 |
| Example 3 | 90.2 | 7.8 | 88.4 | 8.4 | 86.1 | 10.0 |
| Comparative example 1 | 74.3 | 32.3 | 30.8 | 50.2 | 5.8 | 64.8 |

EXAMPLE 4

0.190 Gram of $RuCl_3 \cdot 3H_2O$ was added to a 500 c.c. eggplant-form flask and dissolved with addition of 200 c.c. of water.

was carried out according to the same procedure as in Example 4. The results are shown in Table 2.

TABLE 2

|  | First reaction | | Fifth reaction | | Tenth reaction | |
| --- | --- | --- | --- | --- | --- | --- |
|  | Conversion of benzene (%) | Selectivity of cyclo-hexene (%) | Conversion of benzene (%) | Selectivity of cyclo-hexene (%) | Conversion of benzene (%) | Selectivity of cyclo-hexene (%) |
| Example 4 | 74.8 | 33.6 | 72.1 | 35.9 | 67.5 | 36.8 |
| Example 5 | 76.9 | 34.4 | 73.4 | 34.9 | 70.1 | 37.2 |
| Comparative example 2 | 69.6 | 41.8 | 33.3 | 65.4 | 14.2 | 70.3 |

EXAMPLE 6

Fifty c.c. of water was added to a 100 c.c. stainless steel autoclave in which the air was sufficiently replaced by argon in advance, and 0.5 g of $CoSO_4 \cdot 7H_2O$, an additive, was added to dissolve it in the water. Further, 500 mg of the Ru-Co-Cu/$BaSO_4$ catalyst obtained in Comparative Example 1, 0.5 g of $SiO_2$ and 15 c.c. of benzene were added in this order.

Reaction was carried out with stirring at a temperature of 160° C. for 1 hour under a reaction pressure of 4.0 MPa while introducing a hydrogen gas. The results are shown in Table 3.

EXAMPLE 7

The reaction of Example 6 was further repeated 50 times in all, and it was found that the conversion of benzene and selectivity of cyclohexene after 50th reaction were 74.1% and 52.1%, respectively.

EXAMPLE 8

After the 50th reaction of Example 7 was finished, the same reaction was repeated once more for a prolonged reaction time of 80 minutes. As a result, it was found that the conversion of benzene and selectivity of cyclohexene were 88.9% and 42.7%, respectively.

EXAMPLES 9 AND 10

The catalyst life-evaluating test was carried out according to the same procedure as in Example 6 except that each of $TiO_2$ and $Al_2O_3$ (produced by calcination in air at 450° C. for 3 hours) was added in place of $SiO_2$. The results are shown in Table 3.

COMPARATIVE EXAMPLES 3 TO 7

The catalyst life-evaluating test was carried out according to the same procedure as in Example 6 except that $SiO_2$ was not added, and that various metal oxides shown in Table 3 were added in place of $SiO_2$. The results are shown in Table 3.

TABLE 3

| | | First reaction | | Fifth reaction | | Tenth reaction | |
|---|---|---|---|---|---|---|---|
| | Metal oxide | Conversion of benzene (%) | Selectivity of cyclohexene (%) | Conversion of benzene (%) | Selectivity of cyclohexene (%) | Conversion of benzene (%) | Selectivity of cyclohexene (%) |
| Example 6 | $SiO_2$ | 86.4 | 44.9 | 94.9 | 34.8 | 90.0 | 39.7 |
| Example 9 | $TiO_2$ | 54.9 | 60.9 | 50.0 | 64.0 | 48.2 | 65.9 |
| Example 10 | $Al_2O_3$ | 35.0 | 61.3 | 33.9 | 62.1 | 28.8 | 64.3 |
| Comparative example 3 | None | 76.8 | 56.5 | 4.3 | 79.6 | — | — |
| Comparative example 4 | MgO | 62.9 | 38.1 | 23.3 | 50.2 | 8.5 | 63.4 |
| Comparative example 5 | $MnO_2$ | 56.9 | 38.5 | 38.2 | 51.5 | 14.1 | 65.3 |
| Comparative example 6 | $Nb_2O_5$ | 69.8 | 19.4 | 12.3 | 28.6 | 0.9 | 54.3 |
| Comparative example 7 | ZnO | 1.8 | 66.1 | 1.1 | 72.6 | — | — |

What is claimed is:

1. A method for producing cycloolefins by the partial hydrogenation of corresponding aromatic hydrocarbons with a hydrogen gas in the presence of water and a catalyst comprising barium sulfate as a carrier and ruthenium and one or more metals selected from the group consisting of iron, cobalt, silver and copper supported on the carrier, characterized by incorporating one or more metal oxides selected from the group consisting of silicon dioxide, titanium dioxide and aluminum oxide in the reaction system.

2. A method according to claim 1, wherein the metal oxide is incorporated in the reaction system in the form of a carrier together with barium sulfate.

3. A method according to claim 2, wherein the amount of the metal oxide is 0.2 to 4 by weight ratio to barium sulfate.

4. A method according to claim 1, wherein the metal oxide is incorporated in the reaction system separately from the catalyst.

5. A method according to claim 4, wherein the amount of the metal oxide is 0.2 to 10 by weight ratio to the barium sulfate-supported catalyst.

6. A method according to claim 1, wherein the amount of ruthenium supported is 0.01 to 20 wt.% based on the total amount of the carrier and ruthenium.

7. A method according to claim 1 which uses a catalyst comprising ruthenium and iron or cobalt supported on the carrier, the atomic ratio of iron or cobalt to ruthenium being 0.1 to 15.0.

8. A method according to claim 1 which uses a catalyst comprising ruthenium and copper or silver supported on the carrier, the atomic ratio of copper or silver to ruthenium being 0.05 to 5.0.

9. A method according to claim 1, wherein the amount of water added is 0.01 to 10 times by volume ratio to the aromatic hydrocarbon.

10. A method according to claim 1, wherein the reaction temperature is in the range of from 50° to 250° C.

11. A method according to claim 1, wherein the aromatic hydrocarbon is benzene or toluene.

* * * * *